United States Patent [19]

Inoue

[11] 4,110,374
[45] Aug. 29, 1978

[54] PROCESS FOR SEPARATING AND RECOVERING UNREACTED MATERIALS IN UREA SYNTHESIS

[75] Inventor: Shigeru Inoue, Kamakura, Japan

[73] Assignee: Mitsui Toatsu Chemicals Inc., Tokyo, Japan

[21] Appl. No.: 788,689

[22] Filed: Apr. 18, 1977

Related U.S. Application Data

[63] Continuation-in-part of Ser. No. 736,551, Oct. 28, 1976, abandoned.

[51] Int. Cl.² ............................................. C07C 126/02
[52] U.S. Cl. .................................................. 260/555 A
[58] Field of Search .................................... 260/555 A

[56] References Cited

U.S. PATENT DOCUMENTS

| 3,725,210 | 4/1973 | Otsuka et al. ............... 260/555 A |
| 3,824,283 | 7/1974 | Harada et al. ............... 260/555 A |

FOREIGN PATENT DOCUMENTS

67-6019  9/1967  South Africa ........................ 260/555 A

OTHER PUBLICATIONS

Olsen, Unit Processes and Principles of Chem. Eng., 1932 pp. 1-3.

*Primary Examiner*—O. R. Vertiz
*Assistant Examiner*—Thomas W. Roy
*Attorney, Agent, or Firm*—Fisher, Christen & Sabol

[57] ABSTRACT

A urea synthesis effluent is subjected to at least one high pressure decomposition stage and then a low pressure decomposition stage to decompose and recover unreacted materials contained in said effluent for recycle to the urea synthesis. The urea synthesis effluent discharged from a high pressure decomposition stage is cooled to 105° - 170° C. by indirect heat exchange with the urea synthesis effluent in the rectification zone of the low pressure decomposition stage and then is flashed into the top of said rectification zone, whereby the bottom of said rectification zone is heated to 100° - 140° C. and the temperature at the top of said rectification zone is maintained at 60° - 120° C. to minimize the water content in the distillate from the rectification zone.

17 Claims, 2 Drawing Figures

PROCESS FOR SEPARATING AND RECOVERING UNREACTED MATERIALS IN UREA SYNTHESIS

CROSS-REFERENCE TO RELATED APPLICATION

This application is a continuation-in-part of application Ser. No. 736,551 filed Oct. 28, 1976, now abandoned.

BACKGROUND OF THE INVENTION

1. Field of the Invention

The present invention relates to a process for recovering unreacted materials in the effluent from a synthesis of urea from carbon dioxide and ammonia and, more particularly, it relates to an improved process for recovering unreacted materials from a urea synthesis effluent while reducing the amount of moisture entrained in the unreacted ammonia and carbon dioxide separated from the urea synthesis effluent.

2. Description of the Prior Art

In the production of urea, a total solution recycle process is well known which comprises reacting carbon dioxide with ammonia under high temperature and high pressure conditions, conventionally known and recognized by those skilled in the art as urea synthesis temperature and pressure conditions, subjecting the resulting urea synthesis effluent to a plurality of stripping or distillation stages under respective stepwise reduced presures to separate unreacted materials in the form of a gaseous mixture of ammonia, carbon dioxide and water vapor in each of the respective stages, absorbing the gaseous mixture of unreacted materials discharged from the low pressure distillation stage in an absorbent, increasing the pressure of the resulting absorbate stepwise for use as an absorbent for the mixed gas separated in a higher pressure decomposition stage, and recycling to the urea synthesis zone the absorbate discharged from the final highest pressure decomposition stage. The urea synthesis reaction, i.e., the reaction of ammonia with carbon dioxide to form urea and water, is a reversible reaction, so that the yield of urea decreases with an increase of water content in the urea synthesis reaction system. In order to improve the yield of urea, it is necessary to reduce to as small as possible the water content in the absorbate recycled to the urea synthesis zone. For this purpose, the absorption should be conducted under high pressure in the respective absorption stages and by use of a minimum amount of absorbent. Further, the amount of water which is evaporated and entrained in the gaseous mixture of unreacted materials separated in the respective separation stages should preferably be minimized for preventing the absorbate from being diluted. The gaseous mixtures separated in the separation zones under different pressure conditions have different water contents. Of these, the gaseous mixture which is separated in the low pressure separation zone operated under a gauge pressure of $0 - 5$ $kg/cm^2$ has the greatest content of water. Especially when the unreacted materials in the low pressure stage are stripped off with carbon dioxide fed into the bottom of the separation zone of the low pressure decomposition stage in order to completely separate the unreacted materials from the urea synthesis effluent, the water or moisture content in the separated gaseous mixture disadvantageously increases by an amount of water vaporized and entrained in the carbon dioxide. Accordingly, an additional means is required to suppress this increase in water content.

In order to overcome the above disadvantages, there has been proposed in U.S. Pat. No. 3,725,210 a process wherein the temperature at the top of the low pressure rectification zone having a gauge pressure of $0 - 5$ $kg/cm^2$ is maintained at $60° - 120°$ C. and the temperature at the bottom thereof is kept at $100° - 140°$ C. The present invention contemplates providing an improvement in the above process. In the known process, the temperature at the top of the rectification zone is maintained in the range of $60° - 120°$ C. so that it is possible to lower the vapor pressure and to reduce the water content in the gaseous mixture. In order to maintain the top of the rectification zone at such a low temperature, however, the gaseous mixture exhausted from the top of the rectification zone must be fed to a reflux condenser wherein the gaseous mixture is cooled to a temperature of $50° - 100°$ C. to condense the water vapor therein, the condensed water being recycled to the top of the rectification zone. Thus, the heat energy removed upon the reflux condensation results in a loss, increasing the quantity of heat required for heating the separation zone by an amount corresponding to said heat loss.

SUMMARY OF THE INVENTION

It is therefore an object of the present invention to provide a process for efficiently and economically recovering unreacted ammonia and carbon dioxide from a urea synthesis effluent.

It is another object of the present invention to provide a process for preparing urea in high yield while recovering an unreacted mixed gas containing a reduced amount of water from the urea synthesis effluent.

It is a further object of the present invention to provide a process for effectively recovering heat from a urea synthesis effluent for use in separation and recovery of the unreacted materials.

Still further objects will become apparent from the following detailed description taken in conjunction with the drawing, and the following specific examples which, while indicating preferred embodiments of the invention, are given by way of illustration only.

In order to attain the above objects, the present inventor has made intensive studies on these problems and found that the water content in the gaseous mixture of unreacted materials separated in the low pressure separation stage can be reduced to a certain extent sufficiently by using the heat contained in the urea synthesis effluent.

It has been found that the above objects can be attained by an improvement in the total solution recycle urea synthesis process which includes the steps of reacting in a urea synthesis zone carbon dioxide with ammonia under urea synthesis temperature and pressure conditions, i.e., at a temperature of about $180° - 210°$ C. and under a pressure of about $200 - 260$ $kg/cm^2$ (gauge), to obtain a urea synthesis effluent containing urea, an excess of ammonia, unreacted ammonium carbamate and water, subjecting said urea synthesis effluent to at least two ammonium carbamate decomposition stages including at least one high pressure stage at a gauge pressure above $10$ $kg/cm^2$ and a low pressure stage at a gauge pressure below $5$ $kg/cm^2$ to separate from said urea synthesis effluent gaseous mixtures each composed of ammonia, carbon dioxide and water vapor in the respective separation zones of said high pressure and low pressure decomposition stages, at least a portion of the separation zone of the low pressure stage being a rectification zone having a top and a bottom, contacting each of said gaseous mixtures with an absorbent in absorption zones each of which has substantially the same pressure as that of each of the corresponding separation zones to absorb said gaseous mixtures in said absorbent successively, and recycling the thus-obtained absorbate to the urea synthesis zone, the improvement which comprises cooling the urea synthesis effluent from the separation zone of said high pressure stage to a temperature of 105° – 170° C. by indirect heat exchange in a heat exchange zone with the urea synthesis effluent existing in the bottom of the rectification zone of said low pressure stage, reducing the pressure of said cooled urea synthesis effluent to that of the low pressure stage, introducing the thus pressure reduced effluent into the top of the rectification zone and at the same time heating the bottom of said rectification zone by indirect heat exchange in said heat exchange zone and in an additional heating zone to maintain the temperature of the top of the rectification zone at 60° – 120° C. and the temperature of the bottom of the rectification zone at 100° – 140° C.

When the urea synthesis effluent from the at least one high pressure decomposition stage operated under a gauge pressure of 10 – 170 kg/cm$^2$ and at a temperature of 140° – 200° C. is reduced to a gauge pressure of 0 – 5 kg/cm$^2$ for flashing, the temperature thereof is reduced to 90° – 150° C. In this connection, however, when the urea synthesis effluent from the high pressure separation stage is first subjected to an indirect heat exchange with the urea synthesis effluent existing in the bottom of the rectification zone of the low pressure separation stage so as to cool said urea synthesis effluent from the high pressure stage to 100° – 170° C. and is then reduced to a gauge pressure of 0 – 5 kg/cm$^2$ for flashing, its temperature is reduced to 60° – 120° C. The feed of such a low temperature solution to the top of the low pressure rectification zone reduces the temperature at the top of said zone without any loss of heat, thereby ensuring reduction of the water content in the separated gaseous mixture of unreacted materials.

The excess of heat contained in the hot urea synthesis effluent discharged from the high pressure separation stage is used for heating the bottom of the low pressure rectification zone by indirect heat exchange, resulting in a reduction in the amount of steam required for heating the bottom of the low pressure rectification zone. This is because the indirect heat exchange process enables the steam or moisture content in the gaseous mixture separated in the low pressure separation stage to be reduced much more than in the case where the urea synthesis effluent from the high pressure separation zone is directly flashed into the low pressure separation zone. Thus, the amount of latent heat of vaporization required for said reduced amount of moisture is correspondingly reduced, leading to a reduction in the amount of steam necessary for heating the bottom of the low pressure rectification zone to a predetermined temperature.

In order to completely separate unreacted ammonia and carbon dioxide from the urea synthesis effluent in the low pressure separation zone, it is preferred that the separation zone of the low pressure stage be divided into two zones, i.e., a rectification zone and a stripping zone, and that the urea synthesis effluent from the rectification zone is further fed into the stripping zone wherein a stripping gas, e.g., carbon dioxide, is introduced into the bottom thereof to strip from the urea synthesis effluent the residual unreacted materials for feed to the bottom of the rectification zone. In this case, the absolute amount of moisture in the gaseous mixture obtained from the top of the rectification zone is increased by the amount of that entrained in the stripping gas. In order to reduce the increase in the amount of the entrained moisture, the temperature at the top of the rectification zone should be maintained as low as possible. In practice of the present invention, the temperature at the top of the rectification zone is maintained in the range of 60° – 120° C., within which range the temperature is varied depending on the pressure, with the result that increase in the moisture or water content in said mixed gas can be suppressed and kept low even though the unreacted ammonia and carbon dioxide are stripped off by use of the stripping gas such as carbon dioxide. Thus, the total amount of water vapor evaporated and entrained in said mixed gas does not increase considerably in spite of the increased amount of gaseous mixture.

The stripping gas useful in feeding into the bottom of the expelling or stripping zone to separate the unreacted ammonia and carbon dioxide from the urea synthesis effluent is most preferably carbon dioxide due to its high stripping efficiency. That is, carbon dioxide is sufficient when used in only a small amount to strip the unreacted materials, so that the mixed gas discharged from the low pressure separation zone and composed of the carbon dioxide and unreacted materials is correspondingly reduced in amount, with a reduced total amount of entrained water vapor, when compared to procedures using other stripping gases. The carbon dioxide fed into the stripping zone is recovered in the low pressure absorption zone by being absorbed in an absorbent together with the unreacted ammonia and carbon dioxide separated in the rectification zone and the stripping zone. Upon this absorption, the added or fed carbon dioxide serves to reduce the equilibrium pressure of the low pressure absorption zone and this, in turn, makes it possible to reduce the amount of absorbent used in the low pressure absorption zone.

Although carbon dioxide is the preferred stripping gas, other gases which may be used include hydrogen and inert gases such as nitrogen.

When the preferred carbon dioxide is used as the stripping gas, a portion of the starting carbon dioxide is generally used as the stripping carbon dioxide fed into said stripping zone. The carbon dioxide is generally used for said stripping in an amount of 0.01 – 0.2 mol, preferably 0.02 – 0.1 mol, per mol of urea contained in the urea synthesis effluent fed to the stripping zone. When the amount of carbon dioxide is above 0.2 mol, the amount of distilled water is increased. On the other hand, when the amount is below 0.01 mol, the unreacted materials tend not to be stripped completely.

In practice of the present invention, the separation zone of the low pressure stage is composed, as described hereinbefore, of a rectification zone, a heat exchange zone, an additional heating zone and, if desired, a stripping zone. These zones may be either integrally or separately constituted. For example, said rectification zone and said heat exchange zone and/or additional heating zone may be integrally constituted, i.e., the heat exchanger of said heat exchange zone and/or the heat exchanger of said additional heating zone may be built into the bottom zone of the rectification zone. When the stripping zone is used, the rectification zone and the stripping zone are preferably integrally constituted, i.e., the rectification zone in the upper half portion of the separation zone and the expelling or stripping zone is in the lower half portion thereof, and said additional heating zone may be also integrally combined therewith, whereby the heat exchanger of said additional heating zone is built into said separation zone between said rectification zone and said stripping zone.

The rectification zone may be constructed of bubble cap plate columns or other plate columns having functions corresponding thereto such as sieve plate columns, or may be constructed of a packed column having functions similar to those of the above plate columns.

The stripping zone is generally constructed of a packed bed, and the additional heating zone is composed of a multitubular heat exchanger, i.e., a heater of the one pass type, the reboiler type or the falling film type, which is heated with steam or other hot medium.

DESCRIPTION OF THE PREFERRED EMBODIMENTS

The present invention will be particularly described in connection with the accompanying illustrative and non-limiting drawing.

Figure 1:
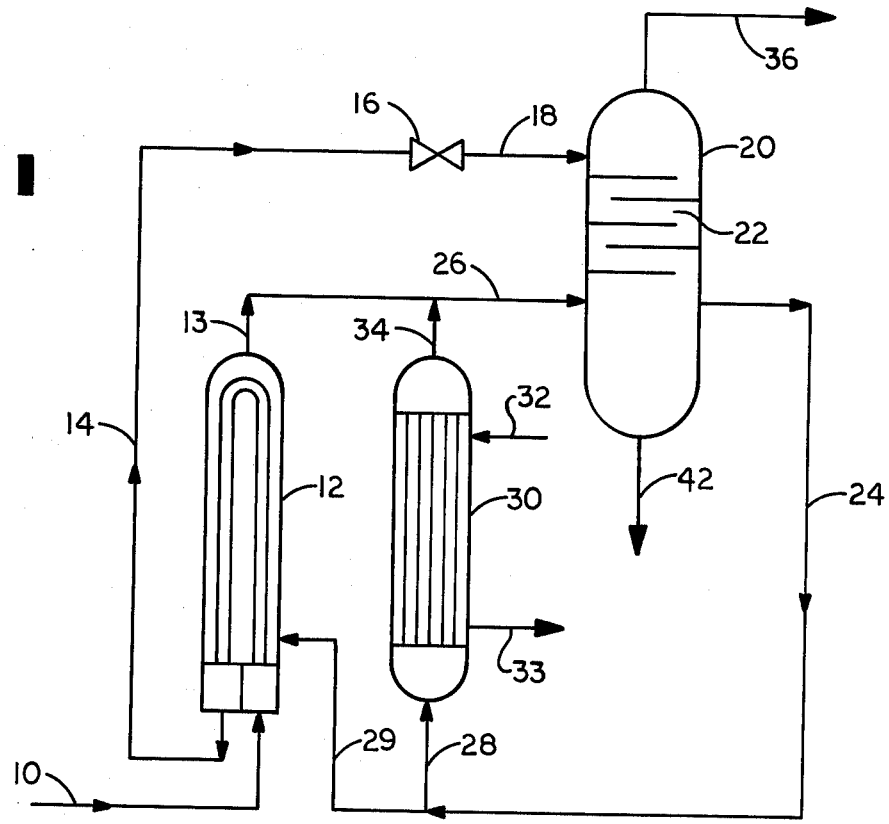
FIG. 1 is a flow chart showing one embodiment of the present invention.

Referring to FIG. 1, a urea synthesis effluent from which the major proportion of unreacted ammonia and carbon dioxide have been separated in a high pressure separation stage (not shown) and discharged from the bottom of the high pressure separation stage or a high pressure distillation tower (not shown) and which has a gauge pressure of 10 – 170 kg/cm$^2$ and a temperature of 140° – 200° C. is fed through line 10 to heat exchanger 12. In heat exchanger 12, the urea synthesis effluent is heat-exchanged with a urea synthesis effluent from the bottom of rectification zone 22 and is cooled to 105° – 170° C. preferably 120° – 150° C. The thus cooled urea synthesis effluent is fed through line 14 through reducing valve 16 wherein its gauge pressure is reduced to 0 – 5 kg/cm$^2$, preferably 1.5 – 3.0 kg/cm$^2$, and is further fed through line 18 to the top of low pressure distillation tower 20 for flashing. By adiabatic expansion, the urea synthesis effluent fed to the top of rectification zone 22 is cooled to 60° – 120° C. The urea synthesis effluent, from which a gaseous mixture of unreacted ammonia, carbon dioxide and water vapor has been separated at the top of rectification zone 22, flows down through the rectification zone to the bottom thereof. Part of the urea synthesis effluent is withdrawn from the bottom of rectification zone 22 through line 24 and fed through line 29 to heat exchanger 12 to be heated by heat exchange with the urea synthesis effluent from the high pressure separation zone. As a result, the heated urea synthesis effluent reaches a temperature of 100° – 140° C., preferably 115° – 135° C., and is recycled to the bottom of rectification zone 22 through lines 13 and 26. Further, a portion of the urea synthesis effluent withdrawn through line 24 is fed through line 28 to reboiler 30 wherein the same is likewise heated to 100° – 140° C., preferably 115° – 135° C., by means of the steam fed through line 32 and exiting through line 33. The thus heated urea synthesis effluent is also recycled to the bottom of rectification zone 22 through line 34 and line 26. The urea synthesis effluent which is recycled from the bottom of rectification zone 22 through heat exchanger 12 and reboiler 30 may be passed through the heat exchanger and reboiler in parallel as shown in FIG. 1. Alternatively, the heat exchanger and the reboiler may be arranged in series (not shown). When the urea synthesis effluent from the bottom of rectification zone 22 is heated in heat exchanger 12 and reboiler 30, most of the unreacted ammonia and carbon dioxide remaining in the urea synthesis effluent are separated in the form of a gaseous mixture and recycled into the bottom of rectification zone 22 together with the urea synthesis effluent. The gaseous mixture is separated therein from the urea synthesis effluent and ascends through rectification zone 22 while condensing a portion of water vapor contained in the gaseous mixture. The mixed gas with reduced water content is exhausted from the top of rectification zone 22 through line 36 together with the gaseous mixture separated by said flashing of the urea synthesis effluent, and fed to a low pressure absorption zone, not shown.

As discussed above, the heat exchanger of the heat exchange zone (heat exchanger 12 of FIG. 1) and/or the additional heating zone (reboiler 30 of FIG. 1) may be built into the bottom zone of the rectification zone (in low pressure distillation tower 20 of FIG. 1). This embodiment is not shown in FIG. 1 but will be readily understood by those skilled in the art.

Figure 2:
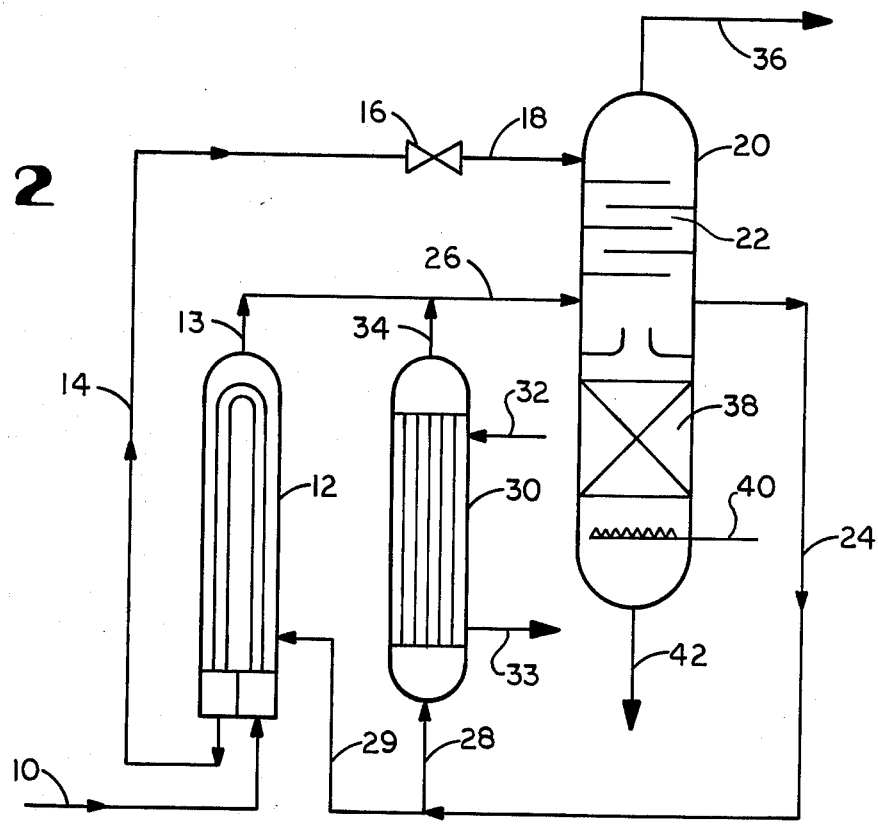
FIG. 2 is a flow chart showing another embodiment of the invention using a stripping treatment with carbon dioxide.

When it is desired to strip the urea synthesis effluent in the bottom of rectification zone 22 by means of carbon dioxide, the urea synthesis effluent is further fed to stripping zone 38 composed of a packed column which is provided in the lower portion of distillation tower 20 as shown in FIG. 2. The urea synthesis effluent descends through stripping zone 38 countercurrently to carbon dioxide which is fed through feed tube 40 provided at the bottom of the stripping zone thereby to separate substantially all of the residual unreacted ammonia and carbon dioxide from the urea synthesis effluent. The thus separated urea synthesis effluent is discharged from the bottom of distillation tower 20 through line 42 to a subsequent concentration step, not shown. The gaseous mixture composed of the carbon dioxide fed to stripping zone 38 and the ammonia and carbon dioxide separated therein is fed from stripping zone 38 to the bottom of rectification zone 22 for mixing therein with the gaseous mixture separated in reboiler 30 and heat exchanger 12. The resulting gaseous mixture ascends through rectification zone 22 and is exhausted from the top thereof through line 36.

As also discussed above, the heat exchanger of the additional heating zone (reboiler 30 of FIG. 2) may be built into the separation zone (low pressure distillation tower of FIG. 2) between the rectification zone and stripping zone. This embodiment is not shown in FIG. 2 but will be readily understood by those skilled in the art.

According to the present invention, the urea synthesis effluent from the high pressure separation stage is first subjected to heat exchange with a urea synthesis effluent existing in the bottom of the rectification zone of the low pressure separation zone to cool said effluent to a predetermined temperature and it is then reduced in pressure, so that the temperature of the urea synthesis effluent is in turn lowered due to adiabatic expansion in a greater degree than that attained by a mere adiabatic expansion technique and, thus, the temperature at the top of the rectification zone can be maintained in a suitable temperature range. In addition, the heat removed by the heat exchange can be used as part of the heat source for heating the bottom of the rectification zone. That is, the heat of the urea synthesis effluent from the high pressure separation zone is caused to be transferred from the top of the low temperature rectification zone to the bottom of the rectification zone with a higher temperature by use of the expansion of the high pressure urea synthesis effluent. Thus, the heat of the hot urea synthesis effluent can be effectively used as a heat source for the rectification. This results in reduction in the amount of steam required for rectification of the urea synthesis effluent in the low pressure decomposition stage. Further, neither a condenser for condensing the water vapor in the gaseous mixture from the top of the rectification tower, nor cooling water for the condenser is required. Additionally, the temperature at the top of the rectification zone is maintained so low that the moisture content in the gaseous mixture of the unreacted materials separated from the rectification zone is reduced and the amount of water recycled to the urea synthesis zone is also reduced, leading to a high yield of urea in the urea synthesis zone.

The present invention will be particularly illustrated by way of the following non-limiting examples.

EXAMPLE 1

As a control test, a urea synthesis effluent withdrawn from the bottom of a high pressure distillation tower operated under a gauge pressure of 19 kg/cm$^2$ at a temperature at the bottom of 180° C. and composed, in kg/hr, of 1130 of urea, 107 of ammonia, 28 of carbon dioxide and 447 of water was flashed, as such, under adiabatic conditions into the top of a low pressure distillation tower operated under a gauge pressure of 2.7 kg/cm$^2$ in accordance with a known process. As a result, a gaseous mixture composed, in kg/hr, of 73.8 of ammonia, 25.4 of carbon dioxide and 53.7 of water was separated from the urea synthesis effluent, and the temperature of the effluent was lowered to 120° C. The urea synthesis effluent obtained after said flashing had a composition composed, in kg/hr, of 1130 of urea, 33.2 of ammonia, 2.6 of carbon dioxide and 393.3 of water. Thereafter, the urea synthesis effluent was further distilled in a distillation tower containing six plates. The resulting solution from the bottom of the tower was heated to 130° C. by means of a reboiler. The urea synthesis effluent discharged from the bottom of the distillation tower contained 2.0 kg/hr of residual ammonia and 1.5 kg/hr of residual carbon dioxide. The mixed gas exhausted from the top of the distillation tower, i.e., a combination of the flashed gas and the gas separated by distillation, had a composition, in kg/hr, of 105 of ammonia, 26.5 of carbon dioxide and 76.4 of water. In the reboiler, 88 kg/hr of 5 kg/cm$^2$ (gauge) steam was consumed.

Then, to show the advantages of the present invention, a urea synthesis effluent discharged from the bottom of the high pressure distillation tower was treated without reducing its pressure in accordance with the process of the invention. That is, said urea synthesis effluent was passed through the tubes of a multi-tubular heat exchanger for heat exchange with a urea synthesis effluent from the bottom of the low pressure distillation tower passed through the shell of said heat exchanger. As a result, the high pressure urea synthesis effluent fed from the heat exchanger was lowered in temperature to 150° C. The urea synthesis effluent was flashed into the top of a low pressure distillation tower operated under a gauge pressure of 2.7 kg/cm$^2$ thereby to separate therefrom a mixed gas composed, in kg/hr, of 56.3 of ammonia, 16.5 of carbon dioxide and 28.3 of water and to lower the effluent temperature to 110° C. The urea synthesis effluent obtained after the flashing contained, in kg/hr, 1130 of urea, 50.7 of ammonia, 11.5 of carbon dioxide and 418.7 of water. The amount of water evaporated upon flashing was reduced to almost half of that attained by the known process by lowering the temperature of the urea synthesis effluent by 30° C. prior to the pressure reduction by the heat exchange. The solution obtained after flashing was distilled in a distillation tower and the resulting solution at the bottom of the tower was heated by means of the aforementioned reboiler and said heat exchanger and maintained at 130° C. As a result, only 2.3 kg/hr of ammonia and 1.7 kg/hr of carbon dioxide remained in the urea synthesis effluent discharged from the bottom of the distillation tower, while the mixed gas exhausted from the top of the distillation tower contained, in kg/hr, 104.7 of ammonia, 26.3 of carbon dioxide and 52.8 of water. Thus, even though the amounts of ammonia and carbon dioxide remaining in said urea synthesis effluent discharged from the bottom of the distillation tower were substantially the same as those in the case of the known process, the total amount of evaporated water was reduced to about 70% of that in the known process. In the process of the invention, only 64 kg/hr of 5 kg/cm$^2$ (gauge) steam was consumed in the reboiler, the steam being reduced by 24 kg/hr when compared with the known process. In other words, the amount of heat required in the reboiler was reduced by an amount corresponding to the difference in amount of evaporated water. Additionally, there was a reduced water content in the absorbate which absorbed the separated gaseous mixture and was recycled to the urea synthesis column, so that the yield of urea was improved.

EXAMPLE 2

The urea synthesis effluent obtained from the distillation tower in Example 1 was further treated in a stripping zone provided beneath the distillation tower in direct connection therewith and composed of a 5 m. high packed bed. Into the bottom of the stripping zone was blown 33 kg/hr of carbon dioxide for stripping. The resulting mixed gas ascended through the stripping zone and also the rectification zone, and was exhausted from the top of the distillation tower together with the flashed gas and the gas separated by the distillation.

When the known process as described in Example 1 without using the heat exchanger of the present invention was combined with this stripping process, the gas exhausted from the top of the distillation tower had a composition, in kg/hr, of 106.0 of ammonia, 60.0 of carbon dioxide and 86.4 of water, and the urea synthesis effluent discharged from the bottom of the packed column contained ammonia and carbon dioxide each in an amount of 1.0 kg/hr.

On the other hand, when the urea synthesis effluent was treated by the process of the present invention combined with said stripping process, the composition of the gas from the top of the distillation tower was composed, in kg/hr, of 105.8 of ammonia, 59.8 of carbon dioxide, and 59.3 of water. The temperature at the bottom of the packed column was 125° C. and the urea synthesis effluent discharged from the bottom of the packed column contained ammonia and carbon dioxide each in an amount of 1.2 kg/hr. Similarly as in Example 1, the amount of evaporated water was reduced to about 70% of that in the case of the known process.

What is claimed is:

1. In a process for recovering unreacted materials and heat from a urea synthesis effluent including the steps of reacting in a urea synthesis zone carbon dioxide with ammonia under urea synthesis temperature and pressure conditions to obtain said urea synthesis effluent containing urea, an excess of ammonia, unreacted ammonium carbamate and water, subjecting said urea synthesis effluent to at least two ammonium carbamate decomposition stages including at least one high pressure steps at a gauge pressure above 10 kg/cm$^2$ and a low pressure stage at a gauge pressure below 5 kg/cm$^2$ to separate from said urea synthesis effluent gaseous mixtures each composed of ammonia, carbon dioxide and water vapor in the respective separation zones of said high pressure and low pressure decomposition stages, at least a portion of the separation zone of the low pressure stage being a rectification zone having a top zone and a bottom zone, contacting each of said gaseous mixtures with an absorbent in absorption zones each of which has substantially the same pressure as that of each of the corresponding separation zones to absorb said gaseous mixtures in said absorbent successively, and recycling the thus-obtained absorbate to the urea synthesis zone, the improvement which comprises cooling the urea synthesis effluent from the separation zone of said high pressure stage to a temperature of 105° – 170° C. by indirect heat exchange in a heat exchange zone with the urea synthesis effluent present in said bottom zone of the rectification zone of said low pressure stage, reducing the pressure of said cooled urea synthesis effluent to that of the low pressure stage, introducing the thus pressure reduced effluent into the top zone of the rectification zone and at the same time heating said urea synthesis effluent present in the bottom zone of said rectification zone by said indirect heat exchange in said heat exchange zone and in an additional heating zone to maintain the temperature of the top zone of the rectification zone at 60° – 120° C. and the temperature of the bottom zone of the rectification zone at 100° – 140° C.

2. The process as claimed in claim 1 wherein said rectification zone is operated under a gauge of from 1.5 to 3.0 kg/cm$^2$.

3. The process as claimed in claim 1 wherein said rectification zone and one or both of said heat exchange zone and said additional heating zone are integrated, whereby the heat exchanger of one or both of said heat exchange zone and additional heating zone is built into said bottom zone of the rectification zone.

4. The process as claimed in claim 1 wherein said rectification zone is a rectification column selected from the group consisting of a bubble cap plate column, a sieve plate column and a packed column.

5. The process as claimed in claim 1 wherein said additional heating zone is a heater indirectly heated with steam and selected from the group consisting of a one pass type, reboiler type and falling film type heat exchanger.

6. The process as claimed in claim 1 wherein said heat exchange zone and said additional heating zone are constituted separately from said rectification zone, and at least a portion of said urea synthesis effluent present in said bottom zone of rectification zone is discharged from said bottom zone, is circulated through said heat exchange zone and additional heating zone to be heated by indirect heat exchange with said urea synthesis effluent from the separation zone of said high pressure stage and is returned to said bottom zone of said rectification zone.

7. The process as claimed in claim 6 wherein said urea synthesis effluent discharged from the bottom of the rectification zone is circulated through said heat exchange zone and said additional heating zone provided in parallel arrangement.

8. The process as claimed in claim 6 wherein said urea synthesis effluent discharged from the bottom of the rectification zone is circulated through said heat exchange zone and said additional heating zone provided in series arrangement.

9. The process as claimed in claim 1 wherein the urea synthesis effluent discharged from said rectification zone is fed to a stripping zone and stripped with a stripping gas to strip off remaining unreacted materials.

10. The process as claimed in claim 9 wherein said stripping zone is a packed column.

11. The process as claimed in claim 9 wherein said stripping gas is carbon dioxide.

12. The process as claimed in claim 11 wherein the amount of said carbon dioxide fed to said stripping zone is from 0.01 to 0.2 mol per mol of urea contained in said urea synthesis effluent treated in the stripping zone.

13. The process as claimed in claim 9 wherein said rectification zone and said stripping zone are integrated whereby said rectification zone is the upper portion of said separation zone and said stripping zone is the lower portion of said separation zone.

14. The process as claimed in claim 13 wherein said rectification zone, said stripping zone and said additional heating zone are integrated, whereby the heat exchanger of said additional heating zone is built into said separation zone between said rectification zone and said stripping zone.

15. The process as claimed in claim 9 wherein said heat exchange zone and said additional heating zone are constituted separately from said rectification zone and said stripping zone, and at least a portion of said urea synthesis effluent present in said bottom zone of rectification zone is discharged from said bottom zone, is circulated through said heat exchange zone and additional heating zone to be heated by indirect heat exchange with said urea synthesis effluent from the separation zone of said high pressure stage and is returned to said bottom zone of said rectification zone.

16. The process as claimed in claim 15 wherein said urea synthesis effluent discharged from the bottom of the rectification zone is circulated through said heat exchange zone and said additional heating zone provided in parallel arrangement.

17. The process as claimed in claim 15 wherein said urea synthesis effluent discharged from the bottom of the rectification zone is circulated through said heat exchange zone and said additional heating zone provided in series arrangement.

* * * * *

UNITED STATES PATENT OFFICE
CERTIFICATE OF CORRECTION

Patent No. 4,110,374          Dated August 29, 1978

Inventor(s) SHIGERU INOUE

It is certified that error appears in the above-identified patent and that said Letters Patent are hereby corrected as shown below:

On the Title page insert:

--{30} Foreign Application Priority Data

March 2, 1976    Japan.....51-21760--

Signed and Sealed this

Sixteenth Day of January 1979

[SEAL]

Attest:

RUTH C. MASON
*Attesting Officer*

DONALD W. BANNER
*Commissioner of Patents and Trademarks*